United States Patent [19]

DiTullio et al.

[11] 3,969,508

[45] July 13, 1976

[54] LOWERING THE CONCENTRATION OF PLASMA TRIGLYCERIDES

[75] Inventors: Nicholas W. DiTullio, Holmes, Pa.; Charles P. Lowman, Cherry Hill, N.J.; Alfred R. Maass, Swarthmore; Harry L. Saunders, Willow Grove, both of Pa.

[73] Assignee: SmithKline Corporation, Philadelphia, Pa.

[22] Filed: Nov. 27, 1974

[21] Appl. No.: 527,560

[52] U.S. Cl................................. 424/275; 424/317
[51] Int. Cl.² ................... A61K 31/19; A61K 31/38
[58] Field of Search ............................ 424/275, 317

[56] References Cited
UNITED STATES PATENTS

| | | | |
|---|---|---|---|
| 3,402,198 | 9/1968 | Bolhofer | 424/317 X |
| 3,758,506 | 9/1973 | Godfroid | 424/275 |

FOREIGN PATENTS OR APPLICATIONS

| | | | |
|---|---|---|---|
| 760,114 | 10/1956 | United Kingdom | 424/317 |
| 1,228,236 | 4/1971 | United Kingdom | 424/317 |

OTHER PUBLICATIONS

Hess, Drugs Affecting Lipid Metab. Adv. Exptl. Med. & Biol. vol. 4 Plenum Press, NY. 1968 pp. 483–489.

*Primary Examiner*—Albert T. Meyers
*Assistant Examiner*—A. P. Fagelson
*Attorney, Agent, or Firm*—Richard D. Foggio; William H. Edgerton

[57] ABSTRACT

Hypolipidemic compositions containing 4-(2-thenoyl)-2,3-dichlorophenoxyacetic acid, its alkali metal salts or pharmaceutically acceptable base addition salts and methods of producing hypolipidemic activity by administering said compound. Combinations with other useful agents are also disclosed.

5 Claims, No Drawings

LOWERING THE CONCENTRATION OF PLASMA TRIGLYCERIDES

This invention relates to novel hypolipidemic compositions containing an active ingredient which lower plasma lipid concentrations and to a method of producing hypolipidemic activity by administering nontoxic effective quantities of said ingredient to hyperlipidemic subjects. More specifically, the active ingredient used in the compositions and methods of this invention is 4-(2-thenoyl)-2,3-dichlorophenoxyacetic acid which has the following formula:

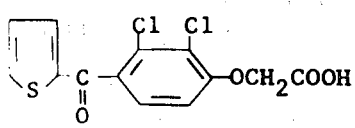

FORMULA-I or an alkali metal salt of said acid, for example the sodium or potassium salt, or a pharmaceutically acceptable addition nontoxic salt of said acid formed with a base, for example the piperazine or (trihydroxymethyl)methylamine salt.

This acid and its preparation is described in U.S. Pat. No. 3,758,506. Generally, 2,3-dichloroanisole is condensed with thiophene-2-carboxylic acid chloride in the presence of aluminum chloride, the resulting ketone is demethylated and the hydroxyketone is reacted with an ester of chloroacetic acid to give the product after hydrolysis of the ester. The compound is disclosed as having diuretic activity.

Abnormal plasma lipid concentrations are a part of coronary heart disease and therefore the reduction of elevated plasma lipids is a desirable goal in the long term management of such disease. The hypolipidemic activity of 4-(2-thenoyl)-2,3-dichlorophenoxyacetic acid or its salts is readily demonstrated in rats by oral administration of the compound at a dose of 300 mg/kg/day for 14 days. On the morning of the fifteenth day, animals are given 150 mg/kg of compound 30 minutes prior to sacrifice. The animals are anesthetized and bled by cardiac puncture. Livers are removed, blotted, weighed and homogenized. Kidneys are excised, decapsulated and weighed. Plasma free fatty acid is analyzed, and plasma and hepatic triglycerides and cholesterol are determined by standard methods.

The results of testing 4-(2-thenoyl)-2,3-dichlorophenoxyacetic acid as described above are summarized in Table I. Compared to controls, the test compound showed a significant decrease in body weight gain, kidney weight was unaffected and liver weight was inreased. Plasma triglycerides were significantly reduced but plasma cholesterol concentrations were not significantly affected, nor was there a significant effect on free fatty acids. Hepatic lipid concentrations are expressed as mg/g liver wet weight and as mg/liver. The test compound did not have a significant effect on hepatic cholesterol when expressed as mg/g liver, however total hepatic cholesterol was increased. Hepatic triglyceride concentration was significantly reduced but total hepatic triglyceride was not affected.

TABLE 1

EFFECT OF 4-(2-THENOYL)-2,3-DICHLOROPHENOXYACETIC ACID
ON BODY WEIGHT GAIN, LIVER WEIGHT, KIDNEY WEIGHT, AND
PLASMA AND HEPATIC LIPID CONCENTRATIONS

| ENDPOINT | CONTROL 0.5% Gum Tragacanth | COMPOUND 150 mg/kg b.i.d. |
|---|---|---|
| INITIAL BODY WEIGHT (g) | 196±7 | 193±6 |
| FINAL BODY WEIGHT (g) | 286±13 | 268±10** |
| BODY WEIGHT GAIN (g) | 90±11 | 74±6*** (−18%) |
| LIVER WEIGHT (g) | 11.8±1.1 | 13.8±1.2** (+17%) |
| KIDNEY WEIGHT | 2.1±0.2 | 2.1±0.1 NS |
| PLASMA LIPIDS | | |
| Cholesterol mg/100 ml | 64±13 | 61±5 NS (−5%) |
| Triglyceride mg/100 ml | 77±33 | 35±15** (−54%) |
| Free Fatty Acids μEq/liter | 338±106 | 287±116 NS (−33%) |
| HEPATIC LIPIDS | | |
| Cholesterol mg/g liver | 2.9±0.1 | 2.8±0.4 NS (−3%) |
| Cholesterol mg/liver | 33.8±3.2 | 38.1±5.4* (+13%) |
| Triglyceride mg/g liver | 5.0±0.7 | 3.9±0.5*** (−22%) |
| Triglyceride mg/liver | 58.8±11.0 | 53.8±9.0 NS (−8%) |

NS = Not significant
*P ≤ 0.05;
**P ≤ 0.01;
***P ≤ 0.001 compared to control group.
Values are X̄±S.D.
Values in parentheses are percent change from control.
10 animals per group.

The hypolipidemic compositions of this invention are prepared in conventional dosage unit forms by incorporating 4-(2-thenoyl)-2,3-dichlorophenoxyacetic acid or a pharmaceutically acceptable salt thereof, in a nontoxic amount sufficient to produce hypolipidemic activity in the designated subject, with a nontoxic pharmaceutical carrier according to accepted procedures. Preferably the compositions will contain the active ingredient in an active but nontoxic amount selected from about 100 mg. to about 500 mg. of active ingredient per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellt form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The method in accordance with this invention comprises administering internally to an animal subject in need of hypolipidemic activity, i.e. a hyperlipidemic subject, the compound 4-(2-thenoyl)-2,3-dichlorophenoxyacetic acid or a salt thereof, usually combined with a pharmaceutical carrier, in a nontoxic amount sufficient to produce hypolipidemic activity. The active ingredient will be administered preferably in a dosage unit, in an active, nontoxic quantity selected from about 100 mg. to about 500 mg. of the parent chemical of Formula I. The route of administration may be orally or parenterally, the oral route being preferred. Advantageously equal doses will be administered two to four times daily with the daily dosage regimen being from about 200 mg. to about 2000 mg. When the method described above is carried out hypolipidemic activity is produced with a minimum of side effects.

The pharmaceutical preparations are made following the conventional techniques of the pharmaceutical chemist involving mixing, granulating and compressing when necessary, or variously mixing and dissolving the ingredients as appropriate to the desired end product.

Also included within the scope of this invention are pharmaceutical compositions comprising 4-(2-thenoyl)-2,3-dichlorophenoxyacetic acid or a salt thereof as described above in combination either with a second active medicinal ingredient used to treat a disease in which hyperlipidemia is a significant component but which agent used to treat the disease or abnormal condition does not reduce the plasma lipid levels of the subject, or with a second hypolipidemic agent. Such diseases and ingredients useful in the combination with the active ingredient of this invention are as follows:

1. Hypertension with associated hyperlipidemia
    a. drugs acting on the afferent sympathetic nervous system
        1. ganglionic blocking agents such as guanethidine
        2. centrally active drugs such as alpha methyldopa, phentolamine or yohimbine and alpha adrenergic blocking agents such as phenoxybenzamine
        3. peripherally and centrally alive drugs such as reserpine and beta adrenergic blocking agents such as propranolol
    b. drugs acting on arteriola smooth muscle such as hydralazine or diazoxide
2. Diabetes with associated hyperlipidemia
hypoglycemic agents such as tolbutamide, chlorpropamide or phenformin
3. Hyperuricemia with associated hyperlipidemia
agents such as allopurinol, probenacid or sulfimpyrazine
4. Hyperlipidemia
agents such as cholestyramine, nicotinamide or para-aminosalicylic acid
5. Hyperlipidemia induced by oral contraceptives
agents such as norethynodrel, norethindrone and acetate, medroxyprogesterone acetate, ethynodiol diacetate, mestranol or ethinyl estradiol
6. Edema treated with potassium sparing diuretics such as spironolactone or triamterene, or hypertension treated with a diuretic such as chlorthalidone.

These combination compositions will contain per dosage unit the same amount of 4-(2-thenoyl)-2,3-dichlorophenoxyacetic acid or a salt thereof as indicated above, namely within the dosage unit range of from about 100 mg. to 500 mg. The amount of the second active ingredient will be the sme dosage set forth for the ingredient in the "Physicians' Desk Reference", 28th Edition, 1974.

Specific examples of combination compositions are as follows:

| 4-(2-Thenoyl)-2,3-dichloro phenoxyacetic acid | Second Active Ingredient | Indication |
|---|---|---|
| 100 mg. to 500 mg. | allopurinol 100 mg. to 300 mg. | hyperuricemia with hyperlipidemia |
| 100 mg. to 500 mg. | cholestyramine 4 g. | hyperlipidemia |
| 100 mg. to 500 mg. | alpha methyldopa 250 mg. | hypertension with hyperlipidemia |
| 100 mg. to 500 mg. | chlorthalidone 50 mg. to 100 mg. | hypertension with hyperlipidemia |
| 100 mg. to 500 mg. | reserpine 0.1 mg. to 1 mg. | hypertension with hyperlipidemia |

The following examples illustrate the preparation of the hypolipidemic compositions of this invention.

| Ingredients | Mg./Tablet |
|---|---|
| 4-(2-Thenoyl)-2,3-dichloro phenoxyacetic acid | 250 |
| Corn starch | 30 |
| Polyvinyl pyrrolidone | 12 |
| Corn starch | 16 |
| Magnesium stearate | 3 |

The first two ingredients are thoroughly mixed and granulated with a 20% w/v solution of polyvinyl pyrrolidone in water. The wetted mass is passed through a No. 4 mesh screen directly onto drying trays. The granules are dried at 50°C. and mixed with the remaining corn starch and magnesium stearate, and compressed into tablets. The tablets are administered to a hyperlipidemic subject 3 times daily.

| Ingredients | Mg./Capsule |
|---|---|
| 4-(2-Thenoyl)-2,3-dichloro phenoxyacetic acid | 500 |
| Magnesium stearate | 2 |
| Lactose | 50 |

The above ingredients are screened through a No. 40 mesh screen, mixed and filled into No. 0 hard gelatin capsules. The capsules are administered to a hyperlipidemic subject twice daily.

What is claimed is:
1. A method of lowering the concentration of plasma triglycerides in a hyperlipidemic subject, which comprises administering internally to said subject a nontoxic amount, sufficient to lower said triglyceride concentration, of the compound 4-(2-thenoyl)-2,3-dichlorophenoxyacetic acid, an alkali metals salt of said acid or a pharmaceutically acceptable addition salt of said acid formed with a base.

2. The method of claim 1 in which a daily dosage of from about 200 mg. to about 2000 mg. of active ingredient is administered.

3. The method of claim 1 in which dosage units containing from about 100 mg. to about 500 mg. of active ingredient are administered from 2 to 4 times daily.

4. The method of claim 1 in which the active ingredient is administered with a pharmaceutical carrier in dosage unit form.

5. The method of claim 4 in which the administration is orally.

* * * * *